United States Patent [19]

Nakai et al.

[11] 4,001,434

[45] Jan. 4, 1977

[54] METHOD OF SLOWING SUBLIMATION OF SUBLIMABLE MATERIAL

[76] Inventors: Yoshinobu Nakai, 2-5-2 Komagome, Toshima, Tokyo; Shin'Ichiro Nakajima, 1-511-5 Tsudanuma, Narashino, Chiba; Yoshimitsu Iida, 1-25-7 Oui, Kija, Tokyo, all of Japan

[22] Filed: Mar. 12, 1975

[21] Appl. No.: 557,870

[30] Foreign Application Priority Data

Sept. 13, 1974 Japan .............................. 49-104900

[52] U.S. Cl. ............................................... 424/361
[51] Int. Cl.$^2$ .......................................... A01N 5/00
[58] Field of Search ..................................... 424/361

[56] References Cited

OTHER PUBLICATIONS

Martin and Cook, Remington's "Pratice of Pharmacy" Mack Publ. Co., Easton, Penn., 1961, p. 134–137 & 158–165.

*Primary Examiner*—Lewis Gotts
*Assistant Examiner*—Cary Owens

[57] ABSTRACT

A method of slowing sublimation of sublimable material comprises mixing the sublimable material with beta-1, 4-glucan and then pulverizing the mixture.

3 Claims, No Drawings

METHOD OF SLOWING SUBLIMATION OF SUBLIMABLE MATERIAL

This invention relates to a method for treatment of sublimable pharmaceuticals, characterized by simultaneously pulverizing beta-1, 4-glucan and a sublimable medicine, whose purpose concerns a method for pharmaceutical manufacture which can control the rate of sublimation.

Ordinarily, where a sublimable material such as camphor is molded by compression independently and used uncovered, it sublimates and scatters in a short time because of its high sublimability and is not fit for prolonged preservation and use.

Consequently in case of using it as insecticide, for example, sublimation is repressed physically by covering its surface with film with pores.

The present invention provides a very varied and effective method for the treatment of sublimable pharmaceuticals which, by using beta-1, 4-glucan as adsorption carrier and/or excipient, improves treatability of the pharmaceuticals, shows rapid release of the pharmaceutical and when the pharmaceutical is put into water for example, controls the rate of sublimation. The method for using cellulose powder as aromatic of perfume is a known fact as described, for example, in "Avicel Review No. 27, page 61 – 67" (published by Asahi Chemical Industry Co., Ltd. Tokyo, April 1972) but this invention comprises completely different technical contents, characterized by simultaneously pulverizing solid sublimable pharmaceuticals and beta-1, 4-glucan.

Also, it is widely known that cellulose powder is mixed with solid aromatic and molded by compression. This invention, characterized by simultaneously pulverizing the mixture of the solid sublimable pharmaceutical concerned and beta-1, 4-glucan, provides supreme effect of sublimation prevention, compared with the ordinary form of usage which provides little effect of sublimation prevention, and is new one based on experimental fact thoroughly unexpected.

This invention was discovered by the following experimental fact:

20 parts of D-camphor, a solid sublimable pharmaceutical, and eighty parts of beta-1, 4-glucan were mixed and 200g of the mixture was put into a 5-liter porcelain ball mill to be simultaneously pulverized. They were pulverized for about six hours until the diffraction peak brought about by the presence of a crystalline substance ceased to appear and the X-ray diffraction diagram became very vague.

In order to examine the sublimability, after the resultant pulverized mixture was maintained in the form of powder at 80° C and at reduced pressure of 5 mm Hg for one hour, the mixture was taken out and it has been demonstrated by examination of the change in weight that only 20% of D-camphor sublimated. Conversely in case obtained by pulverizing beta-1, 4-glucan and D-camphor, independently of each other, and mixing the resultant pulverized materials at the rate by weight of 1:4, the test specimen was treated at 80° C and at pressure of 5 mm Hg for one hour alike, D-camphor sublimated completely.

In the case of a test specimen simultaneously pulverized with beta-1, 4-glucan under the same condition at reduced pressure for two hours, about 70% of D-camphor still remained. D-camphor itself provides inferior solubility in water and therefore, where 10g of the test specimen, obtained by having beta-1, 4-glucan pulverized in advance and mixing it with fine powdered D-camphor, was put into 500 ml of 20° C water, the release rate was only 30% in 10 minutes but in the case of the test specimen obtained by simultaneously pulverizing D-camphor with beta-1, 4-glucan, the release rate was over 90% in 10 minutes, which confirmed the effect of this invention.

Also, 0.5g each of the foregoing two test specimens was charged in a cylindric cast of diameter 8 mm and compressed at pressure of 1 ton/cm$^2$ by using an oil pressure equipment.

The resultant mixture showed excellent tabletability of hardness over 20 kgs and of friability of below 0.5%. Disintegration time in water was 25 minutes. Concerning this tablet, it was found (by a release test of D-camphor in water) that the tablet of test specimen simultaneously pulverized with beta-1, 4-glucan showed the release rate of over 60% in 10 minutes and the higher solubility by six times, compared with the release rate of 10% of the tablet made of powder obtained by, after pulverizing D-camphor and beta-1, 4-glucan, independently of each other, mixing the resultant powder. As regards the method for simultaneous pulverization with beta-1, 4-glucan, though time for pulverization is variable with the particular kind of the pulverizing machine to be used, the amount of the drugs used, the magnitude of power employed for pulverization, etc., it is generally of the order of several hours. The simultaneous pulverization is only required to be continued until the diffraction peak characteristic of a crystalline substance ceases to be detectable in the X-ray diffraction performed by the ordinary reflection method or penetration method.

Any pulverization continued beyond this level only means loss of energy and does not contribute to productivity and rather entails a possibility of degrading the properties of pharmaceuticals being simultaneously pulverized.

If the simultaneous pulverization is stopped before the component pharmaceuticals are completely deprived of crystallinity, namely while the X-ray diffraction peak is still recognizable, the effect aimed at by the present invention is decreased by the extent to which the time of pulverization is curtailed.

As regards the apparatus to be used for the pulverization, it has been confirmed that any mechanism capable of accomplishing required fine pulverization by mechanical crushing or attrition can freely be selected. Examples are a rotary ball mill, a vibrating ball mill, a shaker mill and a hammer mill. The pulverization may be carried out by use of a ball mill of an airtight construction, for example. The atmosphere within the closed ball mill in which the pharmaceuticals are pulverized may be maintained under a continuous flow of such inert gas as nitrogen gas, helium gas or argon gas or said atmosphere may be formed by displacing the interior air of the ball mill in advance with such inert gas. This method is effective to the treatment of pharmaceuticals which are otherwise susceptible to oxidation and other undesirable reactions.

The pulverizing machine tends to run hot, accompanying pulverization. Cooling the body of the pulverizing machine in a known way to prevent the machine from running hot may be adopted as one advantageous measure for working of this invention.

As regards the quantitative relations between beta-1, 4-glucan and drugs to be simultaneously pulverized, the case of D-camphor is described as an instance. As shown in Table 1, the effect of this invention does not change in case a large amount of beta-1, 4-glucan is used, compared with D-camphor, but when beta-1, 4-glucan is less than one fifth of weight of D-camphor, the effect of this invention sharply decreases. Generally speaking, as concerns the treatment of this invention, where more than the same weight of beta-1, 4-glucan was mixed with one weight of the treated pharmaceutical, and simultaneously pulverized, the excellent effect was obtained.

Table 1

| Running hour | Remaining rate of D-camphor (Powder) Mixture rate of D-camphor : beta-1, 4-glucan (rate by weight) | | | | |
|---|---|---|---|---|---|
| | 1:10 | 1:2 | 1:1 | 1:0.2 | 1:0.1 |
| 1 hour | 90 % | 75 % | 60 % | 10 % | 8 % |
| 2 hours | 90 % | 75 % | 60 % | 2 % | 0 % |

Note
(1) condition of treatment : leaving D-camphor as it is at 80° C and at reduced pressure of 5 mm Hg for one hour.
(2) The remaining rate of the control (obtained by merely mixing D-camphor and beta-1, 4-glucan inclusion) had already reached 0 % in one hour.
(3) The release rate of all the test specimens in 20° C water was over 60 % in 10 minutes.
(4) The release rate of the control was 10 % in 10 minutes.

The possible sublimation prevention which is brought about by the simultaneous pulverization of the pharmaceuticals with beta-1, 4-glucan may be explained by a postulate such as is given herein below.

Namely, as a result of the fact that the crystalline structure of the crystal phase in beta-1, 4-glucan is slackened by the mechanical beating force to bring fine pores of 40 – 50A, beta-1, 4-glucan holds the sublimable pharmaceutical in these pores, aside from an increase in adsorption quantity due to an increase of the specific surface area by comminuting the pharmaceuticals and as a result of coupling these sublimable pharmaceuticals with the surface of beta-1, 4-glucan by semi-chemical cohesion, the parmaceutical is believed not to sublimate even by heating at reduced pressure. The reason that after pulverizing beta-1, 4-glucan independently, uniformly mixing the resultant pulverized beta-1, 4-glucan with comminuted sublimable pharmaceutical does not show any effect of sublimation prevention is surmised to be ascribable to the fact that the newly produced surface has a poor ability of strongly adsorbing the sublimable pharmaceutical concerned, through the surface area increases by simply comminiting beta-1, 4-glucan.

It may be also possibly explained that even if the surface has an ability of adsorption, it is nothing but simply physical adsorption or coexistence of beta-1, 4-glucan and a sublimable pharmaceutical. The excellent release effect of the pharmaceutical treated by simultaneous pulverization with beta-1, 4-glucan is believed to be ascribable to increased elimination of the crystallinity of crystalline drugs.

The effect of the present invention was confirmed also concerned other solid sublimable pharmaceuticals such as l-menthol, naphthalene, thymol, etc.

The term "beta-1, 4-glucan" as used in the present invention refers to a product manufactured from a raw material which is a vegetable active ingredient-containing cellulose by means of chemical decomposition, mechanical disintegration, ultrasonic waves, irradiation of high-energy electron beams such as of gamma rays, etc. The chemical decomposition may be carried out by any of the known methods. The mechanical disintegration may freely be accomplished by means of a ball mill, a hammer mill, a tube mill, a vibrating mill or some other crushing or attributing machine in either a wet or dry process. The size reduction of the cellulosic substance by means of ultrasonic waves or by irradiation of high-energy electron beams may be effected by the method suggested by F. M. Morehead (Textile Research Journal, August 1950, pp. 549–553) or by the method proposed by Imamura, Murakami et al (Journal of Textile Science Society, Tokyo, Vol. 15, No. 11, 1959). These methods are not necessarily the only ones that are available for the purpose.

EXAMPLE 1

With 1 kg of beta-1, 4-glucan, 500 g of l-menthol was mixed. The mixture was put into a 20 liter large-sized ball mill and pulverized until the crystalline peak of the simultaneously pulverized pharmaceutical ceased to exist in X-ray diffraction diagram (test specimen A).

Typical conditions adopted for the measurement of X-ray diffraction were as follows:

| Target | Cu | Filter | Ni |
|---|---|---|---|
| Voltage | 30 KV | Current | 10 mA |
| Count range | 250 cps | Time const. | 2 sec. |
| Scanning speed | 2°/min | Chart speed | 40 mm/min. |

Apparatus:
An X-ray diffraction recorder, Model D-F3, made by Rigaku Denki Manufactory, Japan.

As a control, a preparation was obtained by comminuting beta-1, 4-glucan, independently of each other, and mixing the resultant powder at the rate of 2:1 (test specimen B).

Where 10 g each of these test specimens A and B was taken and heated at 80° C and at reduced pressure of 5 mm Hg for one hour, the remaining rates of l-menthol were 80% and 20% respectively by the change of weight.

Where the test specimens were continued to be heated at reduced pressure for one hour more, the remaining rates of 75% and 0% were obtained and the effect of the present invention was observed.

EXAMPLE 2

Confirmation of the ability of sublimation prevention was made by tableting the test specimens A and B obtained in accordance with the "Example 1", by the following method:

A single punch tableting machine with concaves 12 mm in diameter, model 6-B, from Kikusui Manufactory, Japan was used. The product, obtained by adding 0.5 weight % magnesium stearate to each of the test specimens A and B and uniformly mixing them, was compressed. The tablet weight was regulated to 1 g and the tableted product with hardness of over 20 kg was obtained. When both tableted test specimens were heated at reduced pressure in accordance with the "Example 1" the remaining rates of l-menthol of the test specimens A and B were 90% and 25% respectively in an hour and 80% and 0% respectively in 2 hours.

Having thus described the invention, what is claimed is:

1. The method of slowing sublimation of a sublimable pharmaceutical material consisting essentially of mixing the sublimable material with beta-1, 4-glucan, and pulverizing the mixture.

2. The method of claim 1 wherein the weight of beta-1, 4-glucan in the mixture is more than one-fifth the weight of the sublimable material.

3. The method of claim 2 wherein pulverization is carried to the extent that diffraction peak characteristics of a crystalline substance cease to be detectable by X-ray diffraction.

* * * * *

UNITED STATES PATENT OFFICE
CERTIFICATE OF CORRECTION

PATENT NO. : 4,001,434
DATED : January 4, 1977
INVENTOR(S) : Yoshinobu Nakai, Shin'Ichiro Nakajima, and Yoshimitsu Iida It is certified that error appears in the above-identified patent and that said Letters Patent are hereby corrected as shown below:

Cover page, at line designated [76] Inventors:, "Toshima" should read --Toshima-ku--; "Narashino, Chiba" should read --Narashino-City, Chiba Pref.--; "Kija" should read --Kija-ku--. Column 3, Table I, column 1:10 should read --$\geq$90%, $\geq$90%--; column 1:2 should read --$\geq$75%, $\geq$75%--; column 1:1 should read -->60%, >60%--.

Signed and Sealed this

Seventeenth Day of May 1977

[SEAL]

Attest:

RUTH C. MASON
*Attesting Officer*

C. MARSHALL DANN
*Commissioner of Patents and Trademarks*